US00PP35443P2

(12) United States Plant Patent
Weber

(10) Patent No.: US PP35,443 P2
(45) Date of Patent: Oct. 31, 2023

(54) ***VACCINIUM* PLANT NAMED 'DW18-04'**

(50) Latin Name: ***Vaccinium* spp.**
Varietal Denomination: DW18-04

(71) Applicant: Weber Genetics LLC, Winter Haven, FL (US)

(72) Inventor: David Weber, Winter Haven, FL (US)

(73) Assignee: Weber Genetics, Winter Haven, FL (US)

( * ) Notice: Subject to any disclaimer, the term of this patent is extended or adjusted under 35 U.S.C. 154(b) by 0 days.

(21) Appl. No.: 17/954,571

(22) Filed: Sep. 28, 2022

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./156, 157
See application file for complete search history.

*Primary Examiner* — Karen M Redden
(74) *Attorney, Agent, or Firm* — Cassandra Bright

(57) ABSTRACT

A new and distinct cultivar of *Vaccinium* plant named 'DW18-04' is disclosed, characterized by an upright and spreading plant habit, vigorous growth and semi-deciduous habit in Florida. Fruit is very firm, with an average firmness of 333 g/mm. The new variety shows tolerance for wet soil conditions. Fruit yield is exceptionally high, with fruit ripening early, with first harvest in mid-March in Central Florida. Fruit is globose, 18 to 25 mm in diameter with an attractive waxy coating. The new variety is a *Vaccinium*, and is normally used for commercial fruit production.

5 Drawing Sheets

Latin name of the genus and species: *Vaccinium* spp.
Variety denomination: 'DW18-04'.

BACKGROUND OF THE INVENTION

The new cultivar was discovered as the product of a Southern highbush blueberry breeding program conducted in Winter Haven, Fla., by the breeder David Weber. 'DW18-04' was selected from an open pollinated group of seedlings in Winter Haven, Fla. The objective of the breeding program was to develop improved varieties of the seed parent, the low winter chilling requirement *Vaccinium* variety 'Winter Bell', U.S. Plant Pat. No. 27,642. The seed that produced DW 18-04 was collected from open pollinated 'Winter Bell' during March of 2015 from the breeders nursery containing advanced selections from the breeders program. The pollen parent is unknown. 'DW18-04' was selected by the inventor as an interesting new variety in May 2018.

'DW18-04' has been asexually propagated over numerous generations by softwood cuttings in Winter Haven, Fla. and all propagated material has retained the vegetative and fruit characteristics of the mother plant. First asexual propagation was performed June 2018, in Winter Haven, Fla. at a commercial nursery. Vegetative reproduction by cuttings has produced multiple generations, and has shown that the unique features of this cultivar are stable and reproduced true to type through successive generations.

SUMMARY OF THE INVENTION

The cultivar 'DW18-04' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DW18-04.' These characteristics in combination distinguish 'DW18-04' as a new and distinct *Vaccinium* spp. cultivar:

1. Fruit of 'DW18-04' tastes sweeter when harvested before reaching its fully ripe coloration than early harvested fruit of 'Winter Bell'. 'DW18-04' was selected due to its superior flavor characteristics while retaining the best growth, yield and disease tolerant characteristics of its parent.
2. Exhibits excellent leaf retention over winter into spring using the Evergreen Culture method.
3. Produces primocane and floricane fruiting with a large fruit size around 18 mm to 25 mm.
4. Very firm fruit, with an average firmness of 333 g/mm.

PARENT COMPARISON

Plants of the new cultivar 'DW18-04' are similar to plants of the parent variety in most horticultural characteristics. However, plants of the new cultivar 'DW18-04' differ from 'Winter Bell' in the following:

1. Leaf shape of the new variety is more obviate than 'Winter Bell', which is more elliptical.
2. Plant architecture of the new variety is broader with less lateral branching than 'Winter Bell'.
3. Harvest of the new variety is 5-7 days earlier than 'Winter Bell'.
4. Ripe fruit of the new variety has lower acidity, higher Brix compared to 'Winter Bell'. While the acid content has not been measured, taste testing has shown fruit of 'DW18-04' taste sweet, with little acidity even if picked before fruit has reached its fully ripe coloration.

The pollen parent is unknown.

COMMERCIAL COMPARISON

'DW18-04' can be compared to the commercial variety *Vaccinium* 'FL07-399' U.S. Plant Pat. No. 26,313. Plants of the new variety are similar to 'FL07-399' in most horticultural characteristics, however, 'DW18-04' differs in the following:

1. 'FL07-399' is susceptible to bacterial disease *Ralstonia solani*, while 'DW18-04' shows no susceptibility.

'DW18-04' can be compared to the commercial variety *Vaccinium* 'FL01-173' U.S. Plant Pat. No. 21,553. Plants of the new variety are similar to 'FL01-173' in most horticultural characteristics, however, 'DW18-04' differs in the following:

1. Average fruit firmness of 'DW18-04' is 333 g/mm; average fruit firmness of 'FL01-173' is 256 g/mm.

'DW18-04' can be compared to the commercial variety *Vaccinium* 'Avanti' U.S. Plant Pat. No. 26,312. Plants of the new variety are similar to 'Avanti' in most horticultural characteristics, however, 'DW18-04' differs in the following:

1. Typical harvest time of 'Avanti' begins and ends two weeks earlier than 'DW18-04'.
2. 'Avanti' is susceptible to southern red mite (*Tetranychus* spp.) infestation which can severely reduce yield. 'DW18-04' shows no susceptibility to southern red mite (*Tetranychus* spp.).

DEFINITIONS

Terminology below may be useful for description and understanding of the new invention.

Evergreen Culture Method.: A cultural method of sustained winter nutrition used in subtropical climates to delay fall defoliation until the spring leaf flush which can result in an earlier spring harvest.

BRIEF DESCRIPTION OF THE PHOTOGRAPHS

The accompanying photographs illustrate the following:

Figure 1:
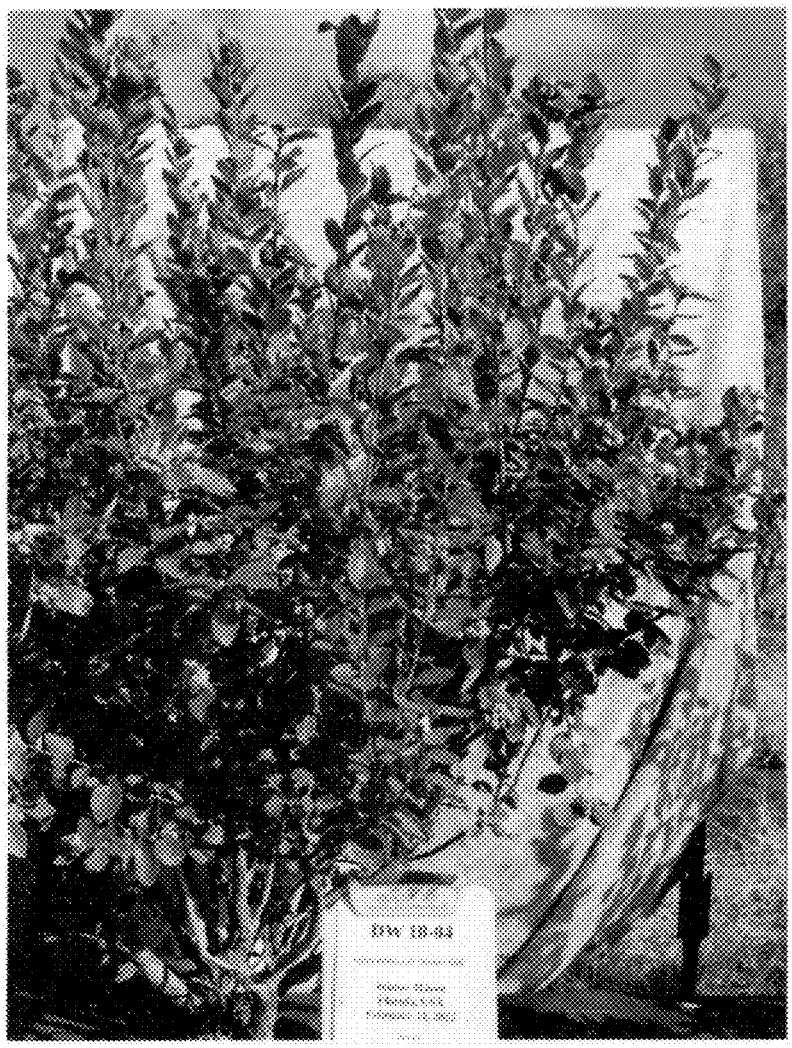
FIG. 1 illustrates in full color a typical plant of 'DW18-04' in February of 2022, grown outdoors in Winter Haven, Fla. This plant is approximately 3 years old.
Figure 2:
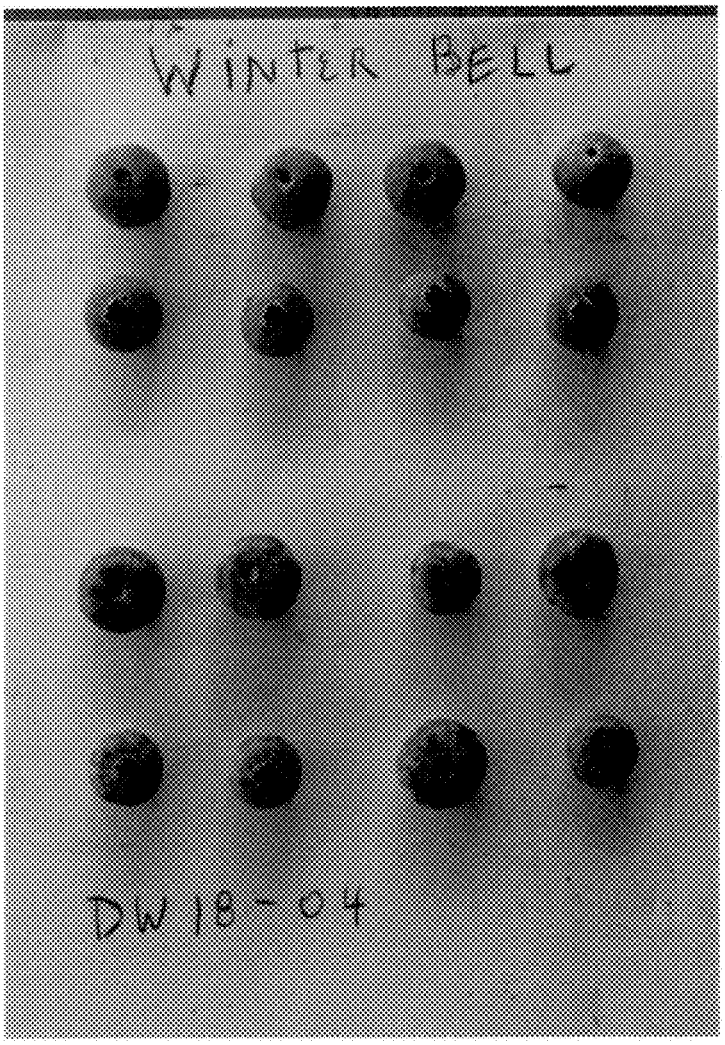
FIG. 2 illustrates in full color typical fruits of 'DW18-04', and typical fruits of 'Winter Bell' during February in Winter Haven, Fla.
Figure 3:
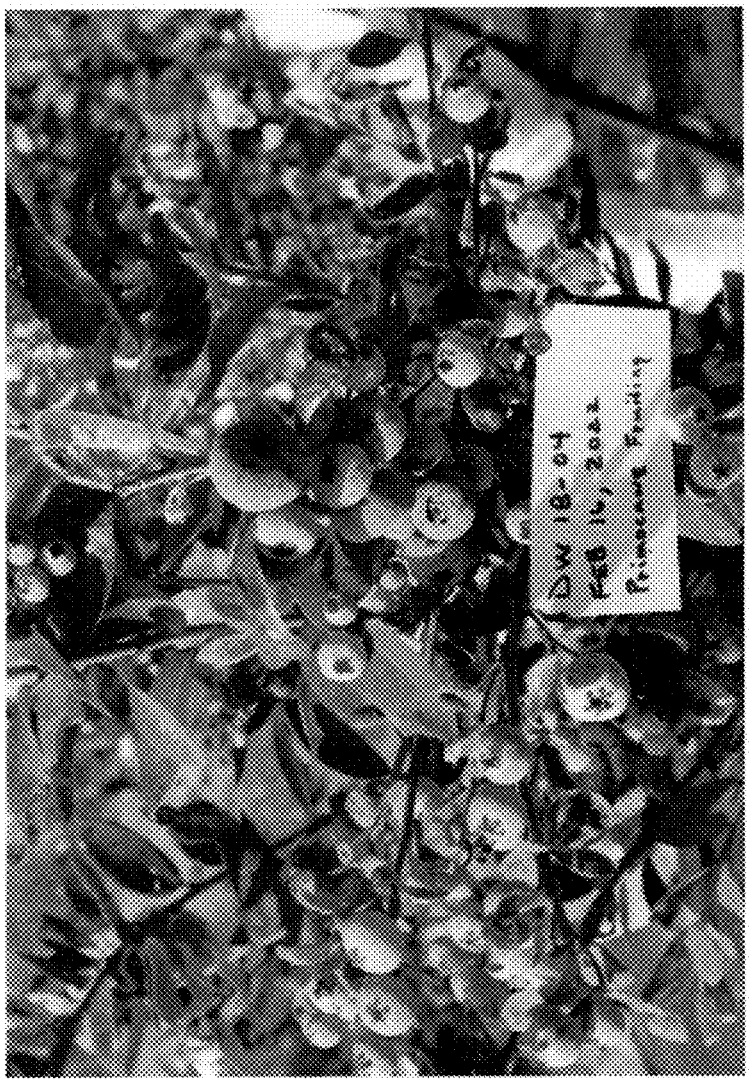
FIG. 3 illustrates in full color primocane fruiting on 'DW18-04' in mid-February in Winter Haven, Fla.
Figure 4:
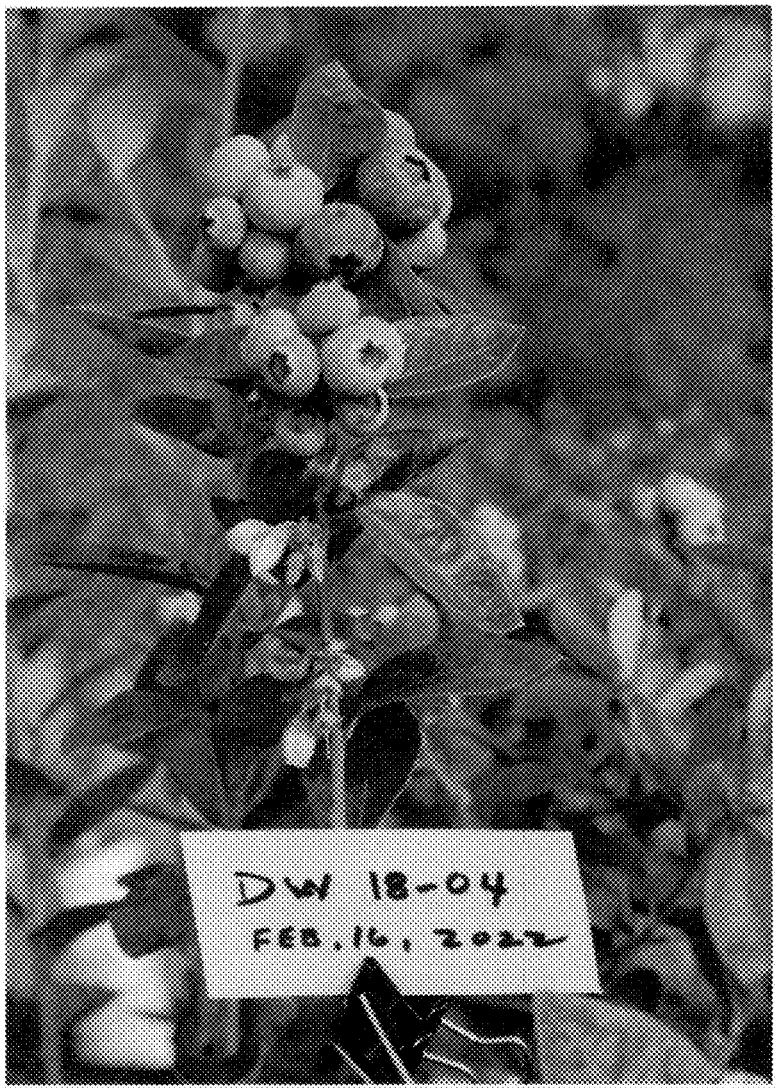
FIG. 4 illustrates in full color typical immature fruit and mature flowers of 'DW18-04' in mid-February in Winter Haven, Fla.
Figure 5:
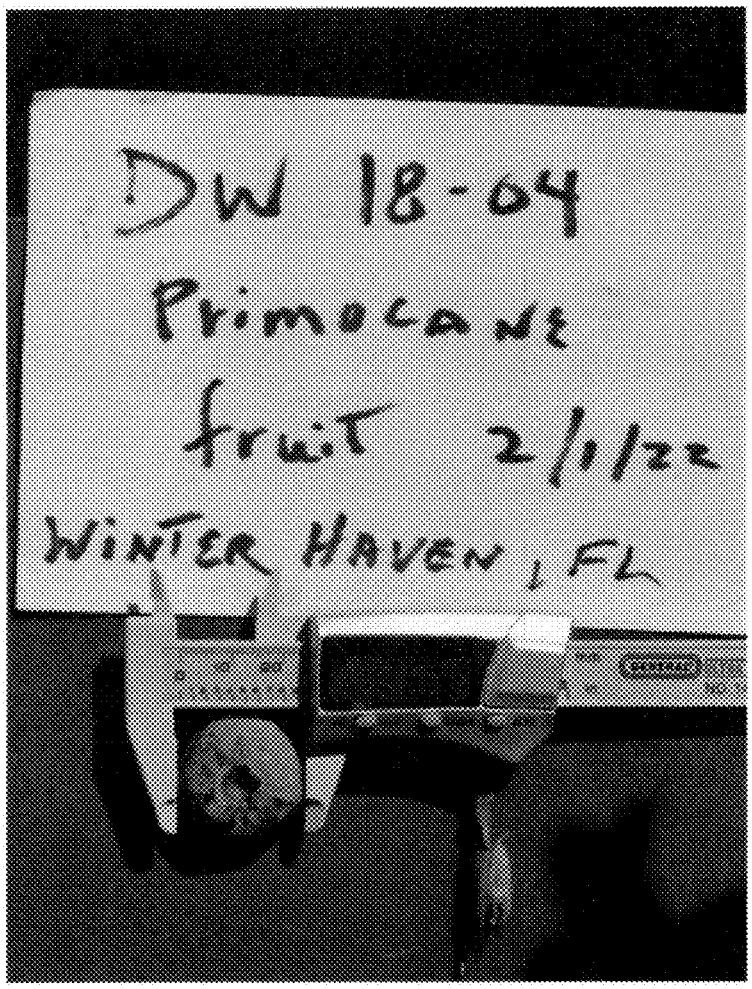

FIG. 5 illustrates in full color a typical fruit of 'DW18-04' harvested Feb. 1, 2022 on primocane in Winter Haven, Fla. The photographs were taken using conventional techniques and although colors may appear different from actual colors due to light reflectance it is as accurate as possible by conventional photographic techniques. Photographs are supplied by the inventor.

DETAILED BOTANICAL DESCRIPTION

In the following description, color references are made to The Royal Horticultural Society Colour Chart 2007 except where general terms of ordinary dictionary significance are used. The following observations and measurements describe 'DW18-04' plants grown outdoors in Winter Haven, Fla. Winter temperature ranged from approximately 38° to 85° F., night and day. Summer temperature night and day range is approximately 65° to 95° F. Measurements and numerical values represent averages of typical flowering types. No chemical or photoperiodic treatments were given.

Botanical classification: *Vaccinium* spp. 'DW18-04'.

Age of plant described: Approximately 5 years old, planted in the ground.

PROPAGATION

Typically from semi-hardwood juvenile cuttings.

Time to rooting: Typically 6 to 8 weeks at 68° to 73° F.

Time to produce a rooted plantlet: Approximately 2 to 3 months.

Rooting habit: Woody to semi-woody. Moderately well branched, colored near RHS Brown 200B.

PLANT

Growth habit: Upright, semi-deciduous woody perennial shrub.

Height: Approximately 1.5 meters.

Plant spread: Approximately 90 cm.

Growth rate: Vigorous.

Branching characteristics: Free branching.

Texture of lateral branches: Smooth.

Color of lateral branches: Near RHS Green 143C.

Aspect: Straight, occurring at approximately 15° to 45° angles.

Strength of lateral branches: Very strong, very flexible.

Vegetative bud burst under evergreen culture method: Spring, typically March or April in Southern United States.

FOLIAGE

Leaf:

*Arrangement.*—Alternate.

*Average length.*—Approximately 7 cm.

*Average width.*—Approximately 4 cm.

*Shape of blade.*—Broad elliptic.

*Apex.*—Acute.

*Base.*—Obtuse.

*Attachment.*—Stalked.

*Margin.*—Entire.

*Texture of top surface.*—Highly waxy, glabrous.

*Texture of bottom surface.*—Highly waxy, glabrous.

*Leaf internode length.*—Approximate range 0.8 cm to 1.5 cm.

*Color.*—Young foliage upper side: Near RHS Yellow-Green 149A. Young foliage under side: Near RHS Yellow-Green 149C. Mature foliage upper side: Near RHS Yellow-Green 140A. Mature foliage under side: Near RHS Yellow-Green 149C.

*Venation.*—Type: Pinnate. Venation color upperside: Near RHS Yellow-Green 149C. Venation color underside: Near RHS Yellow-Green 149C.

*Petiole.*—Length: Approximately 0.2 to 0.6 cm. Diameter: Approximately 0.2 cm. Texture: Smooth. Color upperside: Near RHS Yellow-Green 149B. Color underside: Near RHS Yellow-Green 150C.

FLOWER

Natural flowering season: 50% bloom open in January, in Winter Haven, Fla. Very low chilling or no chilling requirement.

Inflorescence and flower type and habit: Urceolate flowers arrange in small, alternating racemes.
Quantity of flowers per raceme: Approximately 4 to 15 flowers per raceme, variable.
Diameter of raceme: Average approximately 4 to 9 cm.
Depth of raceme: Average approximately 5 to 12 cm.
Fragrance: Not observed.
Bud:
*Shape.*—Obovate.
*Length.*—Approximately 0.4 cm.
*Diameter.*—Approximately 0.3 cm.
*Color.*—Near RHS Yellow-White 158A.
Flower size:
*Diameter.*—Approximately 0.7 cm.
*Length.*—Approximately 10 to 12.5 cm.
*Corolla tube length.*—Approximately 0.6 cm.
*Color tube width.*—Approximately 0.7 cm.
Petals/corolla:
*Quantity.*—5.
*Arrangement.*—Fused.
*Length.*—Approximately 0.6 cm.
*Width.*—Approximately 0.7 cm.
*Shape.*—Completely fused, no individual shape.
*Apex.*—Acute.
*Base.*—Fused.
*Margin.*—Entire.
*Texture, upper and lower surfaces.*—Shiny.
*Color petals and tube.*—When opening, outer surface: Near RHS Yellow-Green 145C. When opening, inner surface: No inner surface exposed. Fully opened, outer surface: Near RHS Yellow-Green 145C. Fully opened, inner surface: No inner surface exposed.
Calyx:
*Sepal quantity.*—5.
*Arrangement.*—Fused.
*Length.*—Approximately 0.4 cm.
*Width.*—Approximately 4 cm.
*Shape.*—Deltoid.
*Apex.*—Acute.
*Base.*—Fused.
*Margin.*—Entire.
*Texture, upper and lower surfaces.*—Matte.
*Color.*—When opening, outer surface: Near RHS Yellow-Green 149B. When opening, inner surface: Not exposed.
Pedicels:
*Length.*—Approximately 0.6 cm.
*Diameter.*—Approximately 0.1 cm.
*Strength.*—Weak to moderate.
*Texture.*—Shiny.
*Color.*—Near RHS Yellow-Green 150A.
Peduncles:
*Length.*—Approximately 0.3 cm.
*Diameter.*—Approximately 0.2 cm.
*Strength.*—Moderate.
*Texture.*—Matte.
*Color.*—Near RHS Yellow-Green 150A.

REPRODUCTIVE ORGANS

Stamens:
*Number.*—Typically 10.
*Color.*—Near RHS Yellow 163D.
*Length.*—Approximately 0.4 cm.
*Anther color.*—Near RHS Yellow 163D.
*Pollen.*—colored near Greyed-Purple N187D.
Pistil:
*Number.*—1.
*Length.*—Approximately 1.2 cm.
*Style.*—Length: Approximately 0.9 cm. Color: Near RHS Yellow-Green 145B.
*Stigma.*—Shape: Narrowly conical. Color: Near RHS Yellow-Green 153D. Ovary Color: Near RHS Yellow-Green 145A.
Fruit:
*Seasonal timing.*—First fruit harvested typically March through April in the Southern United States, including Florida.
*Fruit cluster density.*—Moderate.
*Fruiting habit.*—Fruits on both one-year-old shoots and current season's shoots.
*Color.*—Immature: First near Yellow-Green 145C, changing to Blue 100C. Fully ripe: Colored close to Blue 103A, but much darker, waxy blush coloration near Blue 106D. Ripe internal coloration: Near Yellow-Green 145D.
*Diameter.*—Typical fruit diameter ranges from 18 mm-25 mm.
*Length.*—Average 15 mm.
*Shape.*—Globose.
*Acidity.*—Considerably lower than its parent Winter bell during early ripening. While the acid content has not been measured, taste testing of 'DW18-04' has shown fruit taste sweet, with little acidity even if picked before fruit has reached its fully ripe coloration.
*Sweetness.*—Brix range 11.5-14.

OTHER CHARACTERISTICS

Disease Resistance: Higher than average resistance to foliar diseases normal to *Vaccinium* in Florida, have been observed in this variety. Typical foliar pathogens of *Vaccinium* include rust (*Naohidemyces vaccinii*) and anthracnose leaf spot (*Colletotrichum gloeosporioides*). The new variety appears more resistant to these varieties of foliar pathogens. Resistance to disease found in wet soil conditions also observed. The most common disease found in poorly drained soil is *Phytophthora cinnamomi*, the new variety is likely to have resistance to this pathogen.
Pest resistance: Neither resistance nor susceptibility to the normal pests of *Vaccinium*.
Drought tolerance and temperature tolerance: Low temperature tolerance and drought tolerance have not been tested.

What is claimed is:

1. A new and distinct cultivar of *Vaccinium* plant named 'DW18-04' as herein illustrated and described.

* * * * *